(12) United States Patent
Koch et al.

(10) Patent No.: US 12,329,059 B2
(45) Date of Patent: Jun. 17, 2025

(54) AGRICULTURAL OPERATION MONITORING APPARATUS, SYSTEMS, AND METHODS

(71) Applicant: CLIMATE LLC, Saint Louis, MO (US)

(72) Inventors: Dale Koch, Tremont, IL (US); Brian McMahon, Deer Creek, IL (US); Matt Morgan, Peoria, IL (US); Troy Plattner, Goodfield, IL (US); Jason Stoller, Eureka, IL (US); Mike Strnad, Delavan, IL (US)

(73) Assignee: CLIMATE LLC, Saint Louis, MO (US)

( * ) Notice: Subject to any disclaimer, the term of this patent is extended or adjusted under 35 U.S.C. 154(b) by 0 days.

(21) Appl. No.: 18/238,353

(22) Filed: Aug. 25, 2023

(65) Prior Publication Data
US 2023/0403971 A1     Dec. 21, 2023

Related U.S. Application Data

(63) Continuation of application No. 16/902,265, filed on Jun. 16, 2020, now Pat. No. 11,737,386, which is a
(Continued)

(51) Int. Cl.
*A01C 5/06* (2006.01)
*A01B 47/00* (2006.01)
(Continued)

(52) U.S. Cl.
CPC .............. *A01C 7/201* (2013.01); *A01B 47/00* (2013.01); *A01C 5/068* (2013.01); *A01C 21/007* (2013.01);
(Continued)

(58) Field of Classification Search
CPC ......... A01C 5/062; A01C 5/064; A01C 5/068; A01B 47/00
See application file for complete search history.

(56) References Cited

U.S. PATENT DOCUMENTS 1,921,885 A     8/1933   Kriegbaum et al.
4,023,507 A *   5/1977   van der Lely ....... A01C 23/027
                                                     239/289
(Continued)

FOREIGN PATENT DOCUMENTS

CA      2905119      9/2014
DE      10349321     5/2005
(Continued)

OTHER PUBLICATIONS

U.S. Appl. No. 16/902,265, filed Jun. 16, 2020, Morgan et al.
(Continued)

*Primary Examiner* — Alicia Torres
(74) *Attorney, Agent, or Firm* — Harness, Dickey & Pierce, P.L.C.

(57) ABSTRACT

A system for measuring soil properties has at least one sensor coupled to a row unit of an agricultural implement and a camera coupled to the row unit of the agricultural implement. The at least one sensor is configured to measure at least one soil property of soil worked by the row unit and/or of soil in a trench opened by an opening assembly of the row unit. And, the camera is arranged, on the row unit, to capture images of the soil worked by the row unit and/or the trench opened by the opening assembly of the row unit.

17 Claims, 14 Drawing Sheets

Related U.S. Application Data continuation of application No. 15/736,745, filed as application No. PCT/US2016/037702 on Jun. 15, 2016, now Pat. No. 10,681,861.

(60) Provisional application No. 62/279,995, filed on Jan. 18, 2016.

(51) Int. Cl.
| | |
|---|---|
| *A01C 7/20* | (2006.01) |
| *A01C 21/00* | (2006.01) |
| *G01N 21/359* | (2014.01) |
| *G06V 10/60* | (2022.01) |
| *A01B 79/00* | (2006.01) |
| *G01N 21/3554* | (2014.01) |
| *G01N 33/24* | (2006.01) |
| *G06V 10/56* | (2022.01) |

(52) U.S. Cl.
CPC ............ *G01N 21/359* (2013.01); *G06V 10/60* (2022.01); *A01B 79/005* (2013.01); *A01C 7/203* (2013.01); *G01N 21/3554* (2013.01); *G01N 33/24* (2013.01); *G01N 33/245* (2024.05); *G06V 10/56* (2022.01)

(56) References Cited

U.S. PATENT DOCUMENTS

| | | | |
|---|---|---|---|
| 4,333,096 A | 6/1982 | Jenkins | |
| 5,038,040 A | 8/1991 | Funk | |
| 5,887,491 A | 3/1999 | Monson | |
| 6,199,000 B1 | 3/2001 | Keller | |
| 6,608,672 B1 | 8/2003 | Shibusawa | |
| 8,204,689 B2 | 6/2012 | Christy | |
| 8,365,679 B2 | 2/2013 | Landphair | |
| 8,451,449 B2 | 5/2013 | Holland | |
| 8,862,339 B2 * | 10/2014 | Henry | A01B 63/28 |
| | | | 701/50 |
| 8,924,092 B2 * | 12/2014 | Achen | A01C 21/00 |
| | | | 701/50 |
| 9,585,301 B1 * | 3/2017 | Lund | A01C 21/00 |
| 10,681,861 B2 | 6/2020 | Morgan et al. | |
| 11,737,386 B2 | 8/2023 | Morgan et al. | |
| 2002/0024665 A1 | 2/2002 | Masten | |
| 2002/0131046 A1 | 9/2002 | Christy et al. | |
| 2003/0009286 A1 | 1/2003 | Shibusawa | |
| 2003/0016029 A1 | 1/2003 | Schuler | |
| 2003/0229435 A1 | 12/2003 | Van der Lely | |
| 2010/0212558 A1 | 8/2010 | Schaffert | |
| 2011/0102798 A1 | 5/2011 | Holland | |
| 2011/0113996 A1 | 5/2011 | Mariman | |
| 2020/0359559 A1 | 11/2020 | Koch | |

FOREIGN PATENT DOCUMENTS

| | | | | |
|---|---|---|---|---|
| DE | 60319302 | | 2/2009 | |
| EP | 1275282 B1 * | | 4/2009 | ............ A01C 17/001 |
| EP | 2420122 | | 2/2013 | |
| RU | 2537908 | | 1/2015 | |
| WO | WO-2012102667 A1 * | | 8/2012 | ......... A01B 63/1112 |
| WO | WO2014/153157 | | 9/2014 | |

OTHER PUBLICATIONS

U.S. Appl. No. 15/736,745, filed Dec. 14, 2017, Morgan et al.
U.S. Appl. No. 16/902,265: (a) Office Action dated Jan. 3, 2023; and (b) Notice of Allowance dated Apr. 14, 2023.
U.S. Appl. No. 15/736,745: (a) Office Action dated Sep. 20, 2019; (b) Office Action dated Mar. 18, 2020; and (c) Notice of Allowance dated Apr. 2, 2020.
PCT/US2016/0037702: PCT International Search Report and Written Opinion (6 pages) dated Sep. 16, 2016.
EP 16812375.0: Extended European Search Report dated Jun. 6, 2018.
AU 2016278131: Office Action dated May 18, 2020.
BR 1120170271923: Office Action dated Jun. 16, 2020.

* cited by examiner

AGRICULTURAL OPERATION MONITORING APPARATUS, SYSTEMS, AND METHODS

CROSS-REFERENCE TO RELATED APPLICATIONS

This application is a continuation of U.S. patent application Ser. No. 16/902,265, filed on Jun. 16, 2020, which is a continuation of U.S. patent application Ser. No. 15/736,745, filed on Dec. 14, 2017, which is a U.S. National Stage of International Application No. PCT/US2016/037702, filed on Jun. 15, 2016, which claims the benefit of, and priority to, U.S. Provisional Application No. 62/279,995, filed on Jan. 18, 2016. The entire disclosure of each of the above applications is incorporated herein by reference.

BACKGROUND

In recent years, the availability of advanced location-specific agricultural application and measurement systems (used in so-called "precision farming" practices) has increased grower interest in determining spatial variations in soil properties and in varying input application variables (e.g., planting depth) in light of such variations. However, the available mechanisms for measuring properties such as temperature are either not effectively locally made throughout the field or are not made at the same time as an input (e.g. planting) operation.

Thus, there is a need in the art for a method for monitoring soil properties during an agricultural input application.

DESCRIPTION

Depth Control and Soil Monitoring Systems

Figure 1:
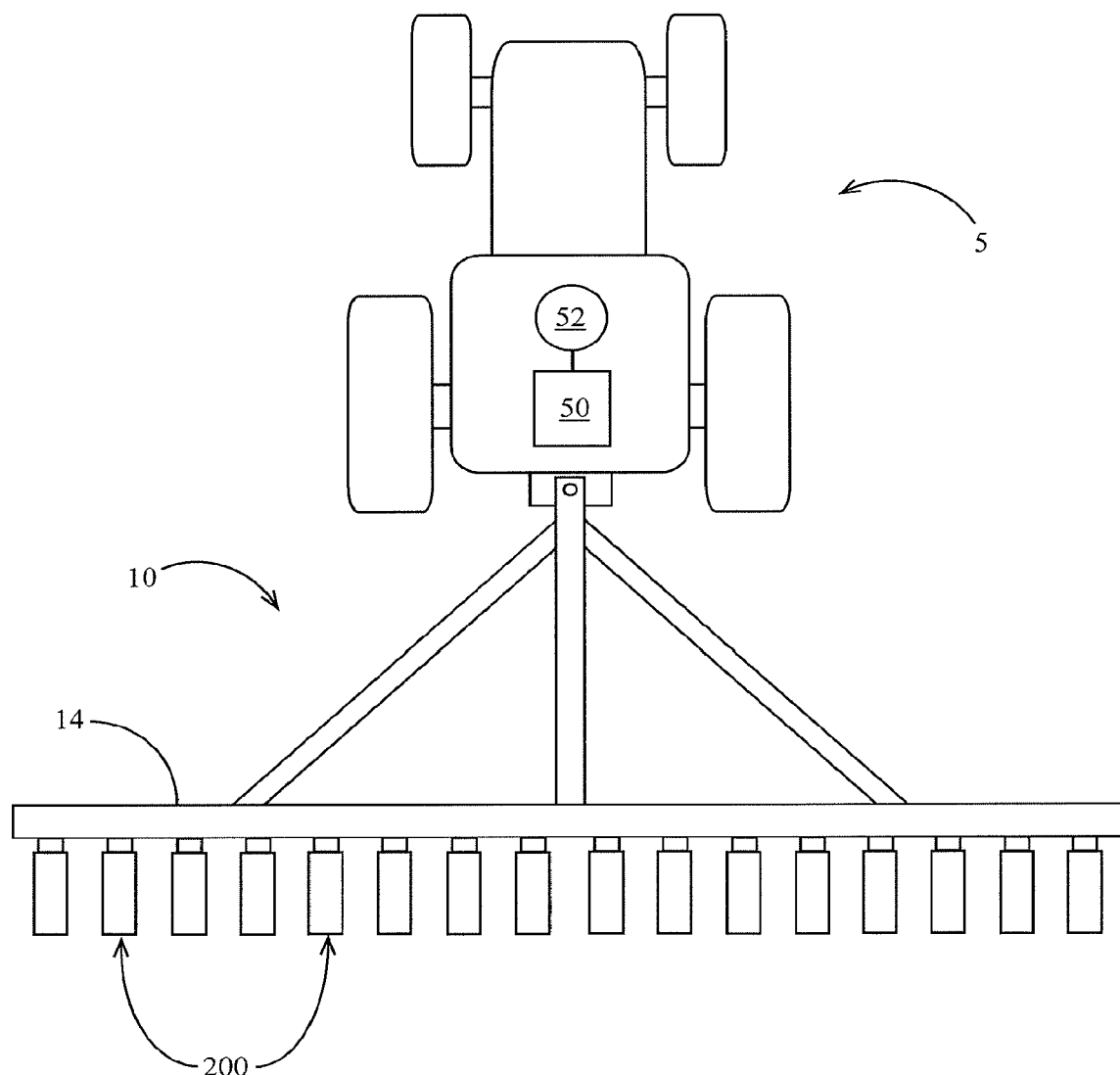
FIG. 1 is a top view of an embodiment of an agricultural planter.

Referring now to the drawings, wherein like reference numerals designate identical or corresponding parts throughout the several views, FIG. 1 illustrates a tractor 5 drawing an agricultural implement, e.g., a planter 10, comprising a toolbar 14 operatively supporting multiple row units 200. An implement monitor 50 preferably including a central processing unit ("CPU"), memory and graphical user interface ("GUI") (e.g., a touch-screen interface) is preferably located in the cab of the tractor 5. A global positioning system ("GPS") receiver 52 is preferably mounted to the tractor 5.

Figure 2:
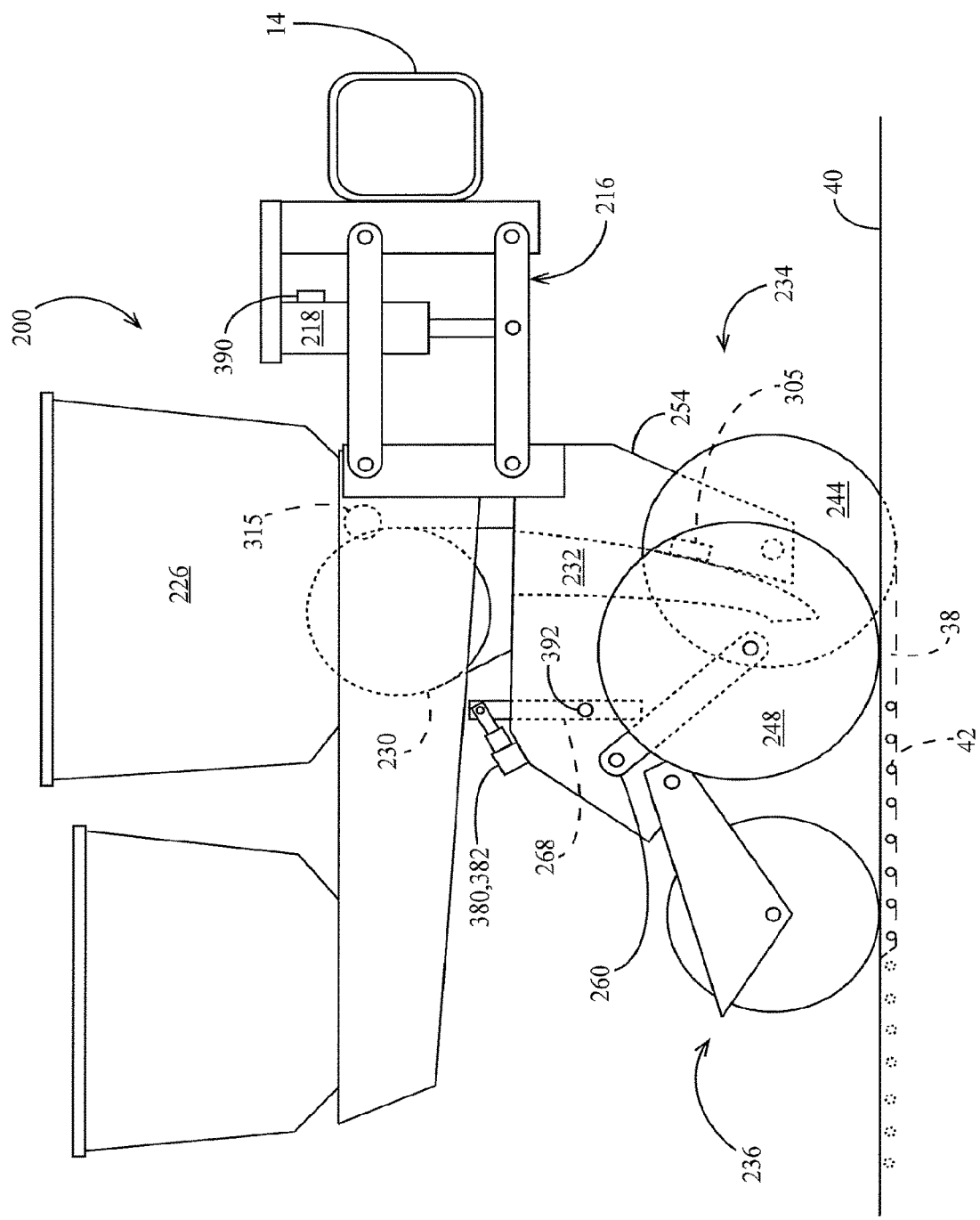
FIG. 2 is a side elevation view of an embodiment of a planter row unit.

Turing to FIG. 2, an embodiment is illustrated in which the row unit 200 is a planter row unit. The row unit 200 is preferably pivotally connected to the toolbar 14 by a parallel linkage 216. An actuator 218 is preferably disposed to apply lift and/or downforce on the row unit 200. A solenoid valve 390 is preferably in fluid communication with the actuator 218 for modifying the lift and/or downforce applied by the actuator. An opening system 234 preferably includes two opening discs 244 rollingly mounted to a downwardly-extending shank 254 and disposed to open av-shaped trench 38 in the soil surface 40. A pair of gauge wheels 248 is pivotally supported by a pair of corresponding gauge wheel arms 260; the height of the gauge wheels 248 relative to the opening discs 244 sets the depth of the trench 38. A depth adjustment rocker 268 limits the upward travel of the gauge wheel arms 260 and thus the upward travel of the gauge wheels 248. A depth adjustment actuator 380 is preferably configured to modify a position of the depth adjustment rocker 268 and thus the height of the gauge wheels 248. The actuator 380 is preferably a linear actuator mounted to the row unit 200 and pivotally coupled to an upper end of the rocker 268. In some embodiments the depth adjustment actuator 380 comprises a device such as that disclosed in International Patent Application No. PCT/US2012/035585 ("the '585 application"), the disclosure of which is hereby incorporated herein by reference. An encoder 382 is preferably configured to generate a signal related to the linear extension of the actuator 380; it should be appreciated that the linear extension of the actuator 380 is related to the depth of the trench 38 when the gauge wheel arms 260 are in contact with the rocker 268. A downforce sensor 392 is preferably configured to generate a signal related to the amount of force imposed by the gauge wheels 248 on the soil surface 40; in some embodiments the downforce sensor 392 comprises an instrumented pin about which the rocker 268 is pivotally coupled to the row unit 200, such as those instrumented pins disclosed in Applicant's U.S. patent application Ser. No. 12/522,253 (Pub. No. US 2010/0180695), the disclosure of which is hereby incorporated herein by reference. Additionally, desired downforce can be achieved by the system and methods for downforce control disclosed in U.S. Pat. Nos. 9,288,937 and 9,144,189, the disclose of each are hereby incorporated herein by reference.

Continuing to refer to FIG. 2, a seed meter 230 such as that disclosed in Applicant's International Patent Application No PCT/US2012/030192, the disclosure of which is hereby incorporated herein by reference, is preferably disposed to deposit seeds 42 from a hopper 226 into the trench 38, e.g., through a seed tube 232 disposed to guide the seeds toward the trench. In some embodiments, the meter is powered by an electric drive 315 configured to drive a seed disc within the seed meter. In other embodiments, the drive 315 may comprise a hydraulic drive configured to drive the seed disc. A seed sensor 305 (e.g., an optical or electromagnetic seed sensor configured to generate a signal indicating passage of a seed) is preferably mounted to the seed tube 232 and disposed to send light or electromagnetic waves across the path of seeds 42. A closing system 236 including one or more closing wheels is pivotally coupled to the row unit 200 and configured to close the trench 38.

Figure 3:
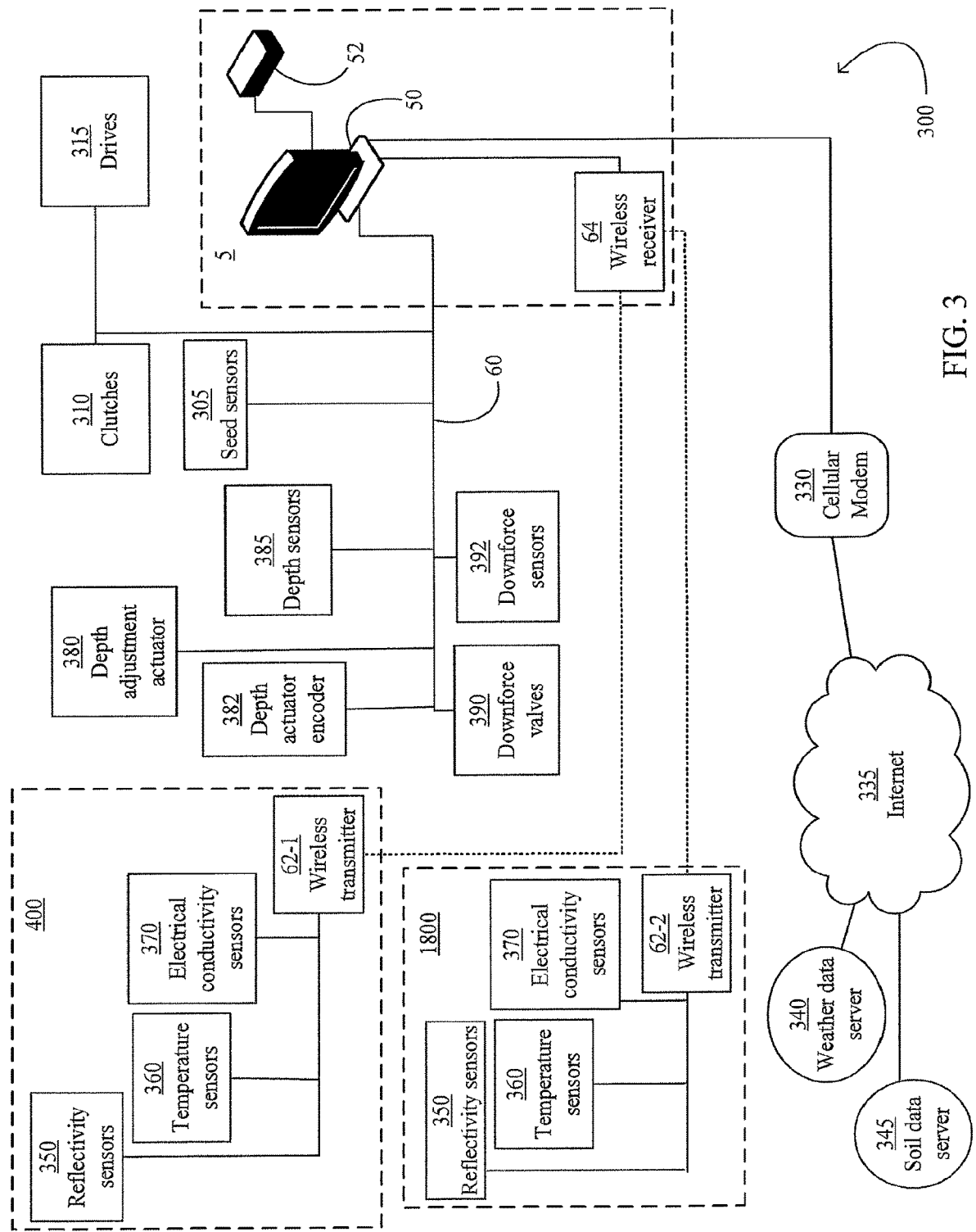
FIG. 3 schematically illustrates an embodiment of a soil monitoring system.

Turning to FIG. 3, a depth control and soil monitoring system 300 is schematically illustrated. The monitor 50 is preferably in data communication with components associated with each row unit 200 including the drives 315, the seed sensors 305, the GPS receiver 52, the downforce sensors 392, the downforce valves 390, the depth adjustment actuator 380, and the depth actuator encoders 382. In some embodiments, particularly those in which each seed meter 230 is not driven by an individual drive 315, the monitor 50 is also preferably in data communication with clutches 310 configured to selectively operably couple the seed meter 230 to the drive 315.

Continuing to refer to FIG. 3, the monitor 50 is preferably in data communication with a cellular modem 330 or other component configured to place the monitor 50 in data communication with the Internet, indicated by reference numeral 335. Via the Internet connection, the monitor 50 preferably receives data from a weather data server 340 and a soil data server 345.

Continuing to refer to FIG. 3, the monitor 50 is also preferably in data communication with one or more temperature sensors 360 mounted to the planter 10 and configured to generate a signal related to the temperature of soil being worked by the planter row units 200. The monitor 50 is preferably in data communication with one or more reflectivity sensors 350 mounted to the planter 10 and configured to generate a signal related to the reflectivity of soil being worked by the planter row units 200.

Referring to FIG. 3, the monitor 50 is preferably in data communication with one or more electrical conductivity sensors 370 mounted to the planter 10 and configured to generate a signal related to the temperature of soil being worked by the planter row units 200.

In some embodiments, a first set of reflectivity sensors 350, temperature sensors 360, and electrical conductivity sensors 370 are mounted to a soil engaging component 400, such as a seed firmer, disposed to measure reflectivity, temperature and electrical conductivity, respectively, of soil in the trench 38. In some embodiments, a second set of reflectivity sensors 350, temperature sensors 360, and electrical conductivity sensors 370 are mounted to a reference sensor assembly 1800 and disposed to measure reflectivity, temperature and electrical conductivity, respectively, of the soil, preferably at a depth different than the sensors on the seed firmer 400.

In some embodiments, a subset of the sensors are in data communication with the monitor 50 via a bus 60 (e.g., a CAN bus). In some embodiments, the sensors mounted to the seed firmer 400 and the reference sensor assembly 1800 are likewise in data communication with the monitor 50 via the bus 60. However, in the embodiment illustrated in FIG. 3, the sensors mounted to the seed firmer the sensors mounted to the seed firmer 400 and the reference sensor assembly 1800 are in data communication with the monitor 50 via a first wireless transmitter 62-1 and a second wireless transmitter 62-2, respectively. The wireless transmitters 62 at each row unit are preferably in data communication with a single wireless receiver 64 which is in turn in data communication with the monitor 50. The wireless receiver may be mounted to the toolbar 14 or in the cab of the tractor 5.

Soil Monitoring, Seed Monitoring and Seed Firming Apparatus

Figure 4A:
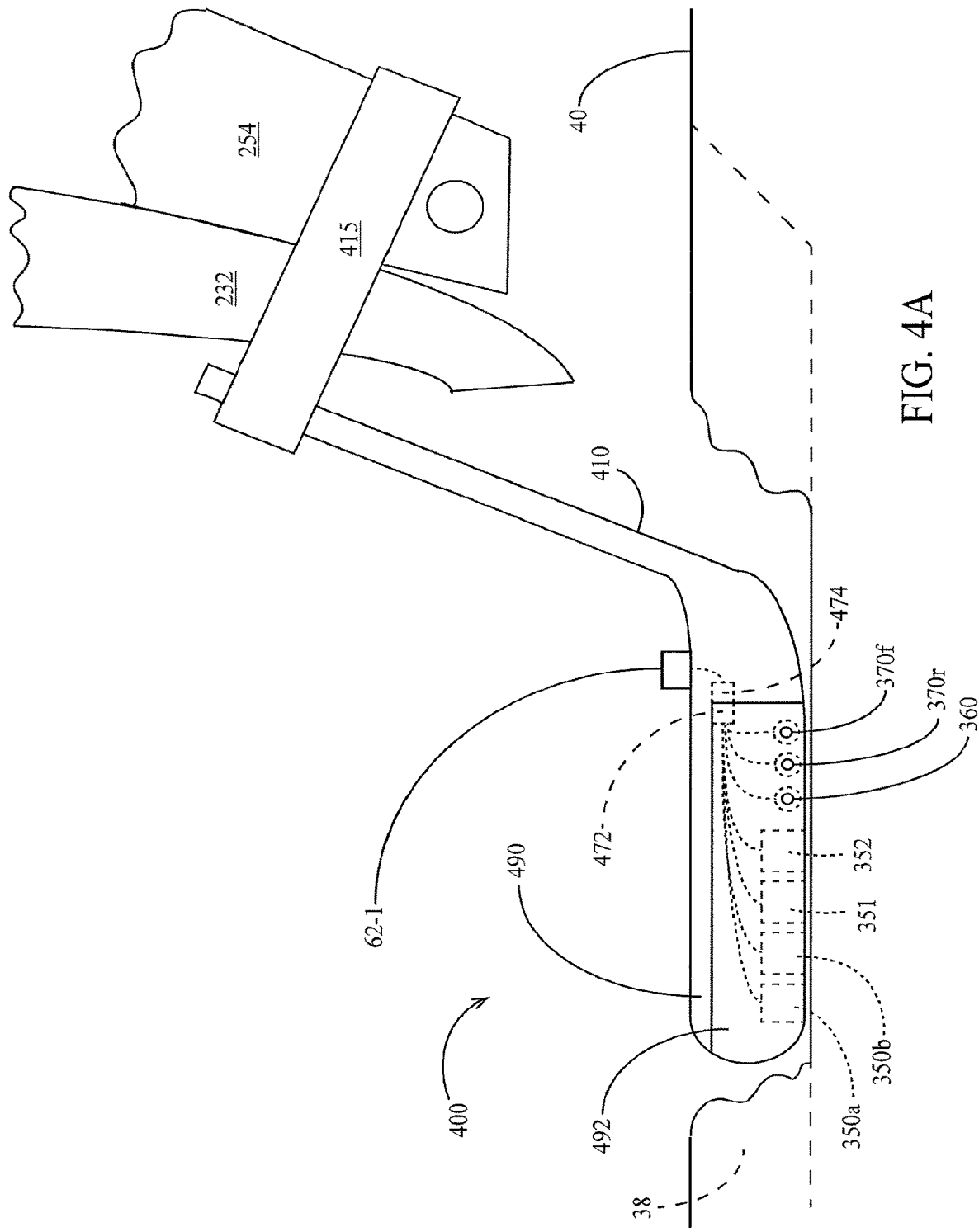
FIG. 4A is a side elevation view of an embodiment of a seed firmer having a plurality of firmer-mounted sensors.
Figure 4B:
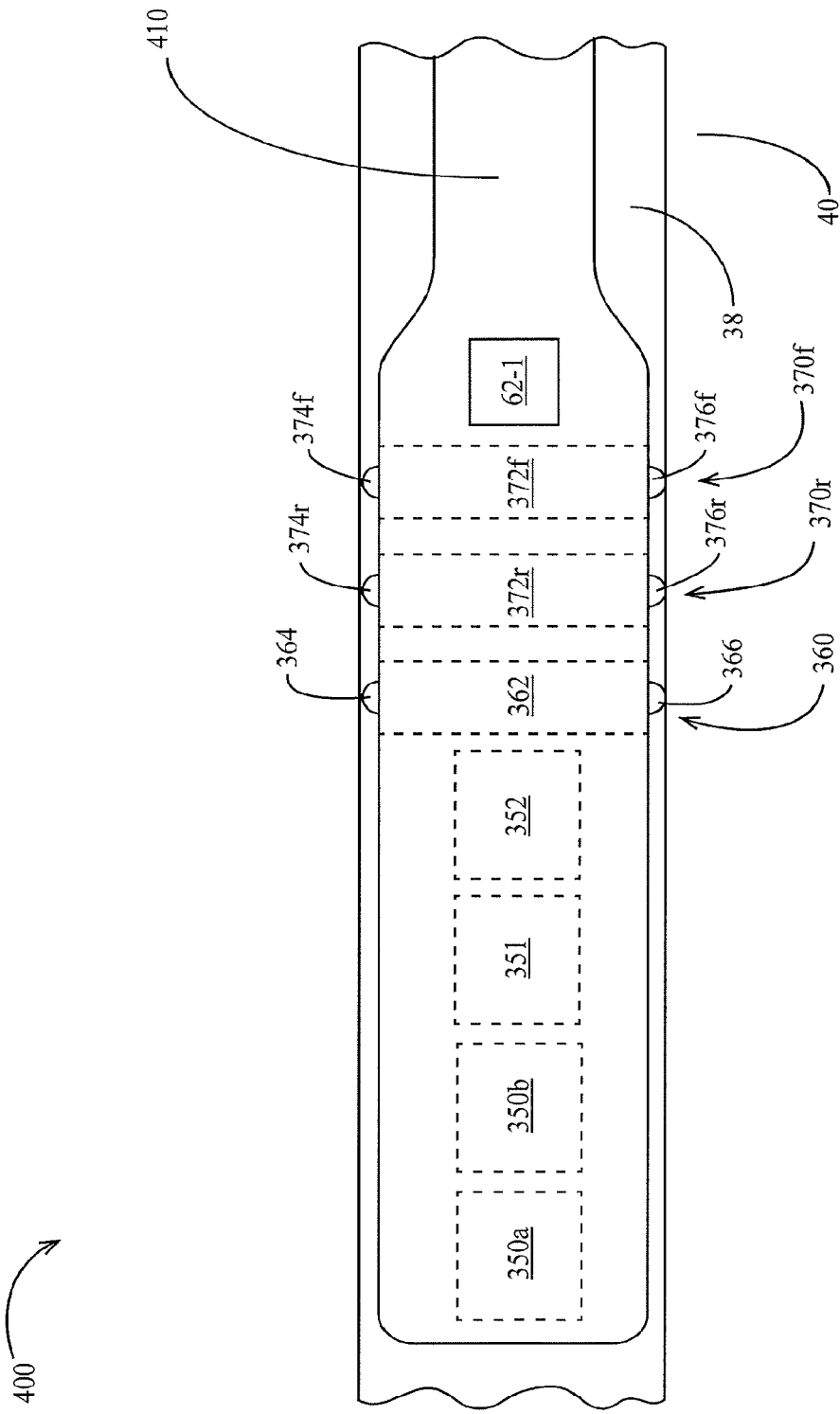
FIG. 4B is a plan view of the seed firmer of FIG. 4A.
Figure 4C:
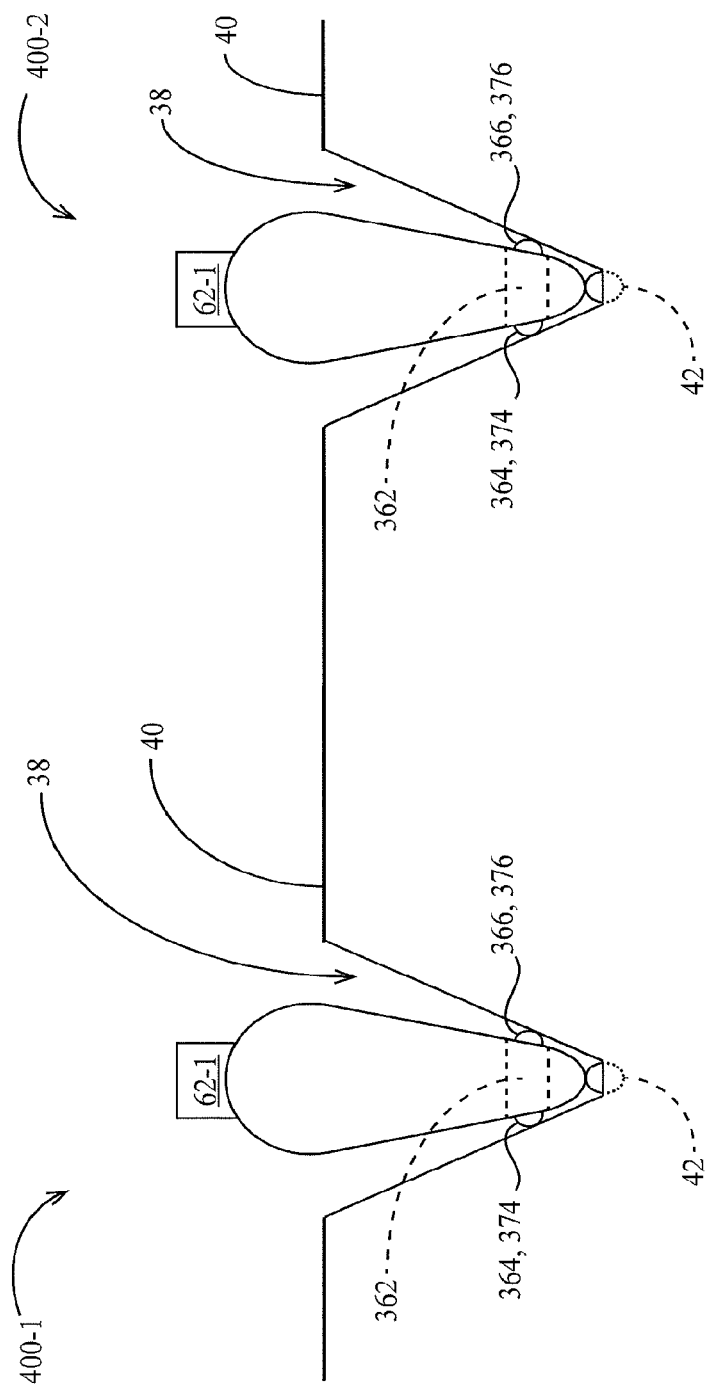
FIG. 4C is a rear elevation view of the seed firmer of FIG. 4A.

Turning to FIGS. 4A-4C, an embodiment of the soil engaging component comprising a seed firmer 400 is illustrated having a plurality of sensors for sensing soil characteristics. The seed firmer 400 preferably includes a flexible portion 410 mounted to the shank 254 and/or the seed tube 232 by a bracket 415. In some embodiments, the bracket 415 is similar to one of the bracket embodiments disclosed in U.S. Pat. No. 6,918,342, incorporated by reference herein. The seed firmer preferably includes a firmer body 490 disposed and configured to be received at least partially within v-shaped trench 38 and firm seeds 42 into the bottom of the trench. When the seed firmer 400 is lowered into the trench 38, the flexible portion 410 preferably urges the firmer body 490 into resilient engagement with the trench. In some embodiments the flexible portion 410 preferably includes an external or internal reinforcement as disclosed in PCT/US2013/066652, incorporated by reference herein. In some embodiments the firmer body 490 includes a removable portion 492; the removable portion 492 preferably slides into locking engagement with the remainder of the firmer body. Alternatively, the removable portion 492 can be attached to firmer body 490 with a removable fastener, such as a screw. The firmer body 490 (preferably including the portion of the firmer body engaging the soil, which in some embodiments comprises the removable portion 492) is preferably made of a material (or has an outer surface or coating) having hydrophobic and/or anti-stick properties, e.g. having a Teflon graphite coating and/or comprising a polymer having a hydrophobic material (e.g., silicone oil or polyether-ether-ketone) impregnated therein. Alternatively, the sensors can be disposed on the side of seed firmer 400 (not shown).

The seed firmer 400 preferably includes a plurality of reflectivity sensors 350a, 350b. Each reflectivity sensor 350 is preferably disposed and configured to measure reflectivity of soil; in a preferred embodiment, the reflectivity sensor 350 is disposed to measure soil in the trench 38, and preferably at the bottom of the trench. The reflectivity sensor 350 preferably includes a lens disposed in the bottom of the firmer body 490 and disposed to engage the soil at the bottom of the trench 38. In some embodiments the reflectivity sensor 350 comprises one of the embodiments disclosed in U.S. Pat. No. 8,204,689 and/or WO2014/186810, both of which are incorporated by reference herein. In various embodiments, the reflectivity sensor 350 is configured to measure reflectivity in the visible range (e.g., 400 and/or 600 nanometers), in the near-infrared range (e.g., 940 nanometers) and/or elsewhere in the infrared range.

The seed firmer 400 also preferably includes a capacitive moisture sensor 351 disposed and configured to measure capacitance moisture of the soil in the seed trench 38, and preferably at the bottom of trench 38.

The seed firmer 400 also preferably includes an electronic tensiometer sensor 352 disposed and configured to measure soil moisture tension of the soil in the seed trench 38, and preferably at the bottom of trench 38.

Alternatively, soil moisture tension can be extrapolated from capacitive moisture measurements or from reflectivity measurements (such as at 1450 nm). This can be done using a soil water characteristic curve based on the soil type.

The seed firmer 400 preferably includes a temperature sensor 360. The temperature sensor 360 is preferably disposed and configured to measure temperature of soil; in a preferred embodiment, the temperature sensor is disposed to measure soil in the trench 38, preferably at or adjacent the bottom of the trench 38. The temperature sensor 360 preferably includes soil-engaging ears 364, 366 disposed to slidingly engage each side of the trench 38 as the planter traverses the field. The ears 364, 366 preferably engage the trench 38 at or adjacent to the bottom of the trench. The ears 364, 366 are preferably made of a thermally conductive material such as copper. The ears 364 are preferably fixed to and in thermal communication with a central portion 362 housed within the firmer body 490. The central portion 362 preferably comprises a thermally conductive material such as copper; in some embodiments the central portion 362 comprises a hollow copper rod. The central portion 362 is preferably in thermal communication with a thermocouple fixed to the central portion.

The seed firmer preferably includes a plurality of electrical conductivity sensors 370r, 370f. Each electrical conductivity sensor 370 is preferably disposed and configured to measure electrical conductivity of soil, in a preferred embodiment, the electrical conductivity sensor is disposed to measure electrical conductivity of soil in the trench 38, preferably at or adjacent the bottom of the trench 38. The electrical conductivity sensor 370 preferably includes soil-engaging ears 374, 376 disposed to slidingly engage each side of the trench 38 as the planter traverses the field. The ears 374, 376 preferably engage the trench 38 at or adjacent to the bottom of the trench. The ears 374, 376 are preferably made of an electrically conductive material such as copper. The ears 374 are preferably fixed to and in electrical communication with a central portion 372 housed within the firmer body 490. The central portion 372 preferably comprises an electrically conductive material such as copper; in some embodiments the central portion 372 comprises a copper rod. The central portion 372 is preferably in electrical communication with an electrical lead fixed to the central portion. The electrical conductivity sensor can measure the electrical conductivity within a trench by measuring the electrical current between soil-engaging ears 374 and 376.

Referring to FIG. 4B, in some embodiments the system 300 measures electrical conductivity of soil adjacent the trench 38 by measuring an electrical potential between the forward electrical conductivity sensor 370f and the rearward electrical conductivity sensor 370r.

Referring to FIG. 4C, in some embodiments the system 300 measures electrical conductivity of soil between two row units 200 having a first seed firmer 400-1 and a second seed firmer 400-2, respectively, by measuring an electrical potential between an electrical conductivity sensor on the first seed firmer 400-1 and an electrical conductivity sensor on the second seed firmer 400-2.

The reflectivity sensors 350, the capacitive moisture sensors 351, the electronic tensiometer sensors 352, the temperature sensors 360, and the electrical conductivity sensors 370 (collectively, the "firmer-mounted sensors") are preferably in data communication with the monitor 50. In some embodiments, the firmer-mounted sensors are in data communication with the monitor 50 via a transceiver (e.g., a CAN transceiver) and the bus 60. In other embodiments, the firmer-mounted sensors are in data communication with the monitor 50 via wireless transmitter 62-1 (preferably mounted to the seed firmer) and wireless receiver 64. In some embodiments, the firmer-mounted sensors are in electrical communication with the wireless transmitter 62-1 (or the transceiver) via a multi-pin connector comprising a male coupler 472 and a female coupler 474. In firmer body embodiments having a removable portion 492, the male coupler 472 is preferably mounted to the removable portion and the female coupler 474 is preferably mounted to the remainder of the firmer body 190; the couplers 472,474 are preferably disposed such that the couplers engage electrically as the removable portion is slidingly mounted to the firmer body.

It should be appreciated that the sensor embodiment of FIGS. 4A-4C may be mounted to and used in conjunction with implements other than seed planters such as tillage tools. For example, the seed firmer could be disposed to contact soil in a trench opened by (or soil surface otherwise passed over by) a tillage implement such as a disc harrow or soil ripper. On such equipment, the sensors could be mounted on a part of the equipment that contacts soil or on any extension that is connected to a part of the equipment and contacts soil. It should be appreciated that in some such embodiments, the seed firmer would not contact planted seed but would still measure and report soil characteristics as otherwise disclosed herein.

Data Processing and Display

Figure 5:
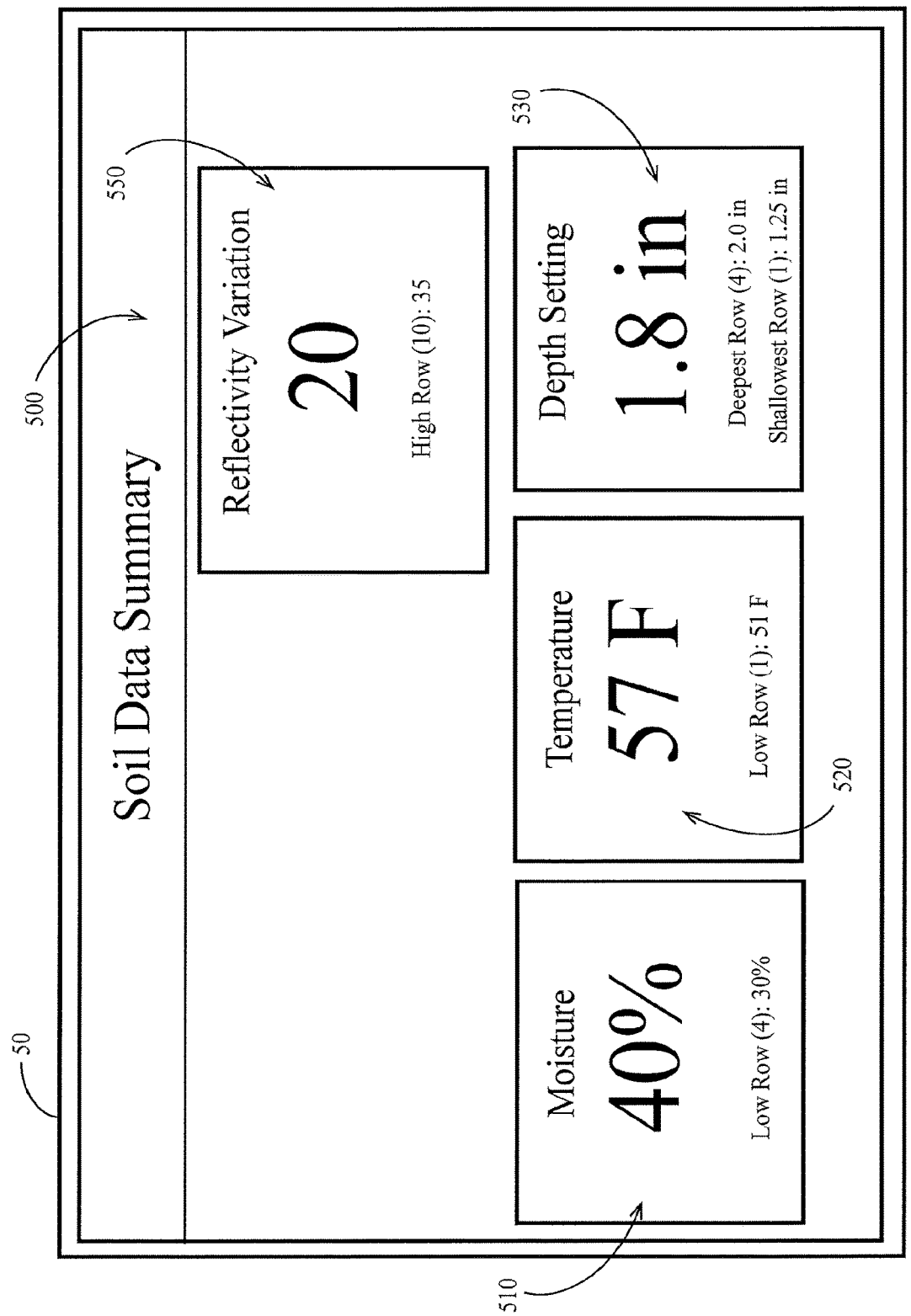
FIG. 5 illustrates an embodiment of a graphical display including a numerical representation of reflectivity variation.
Figure 6:
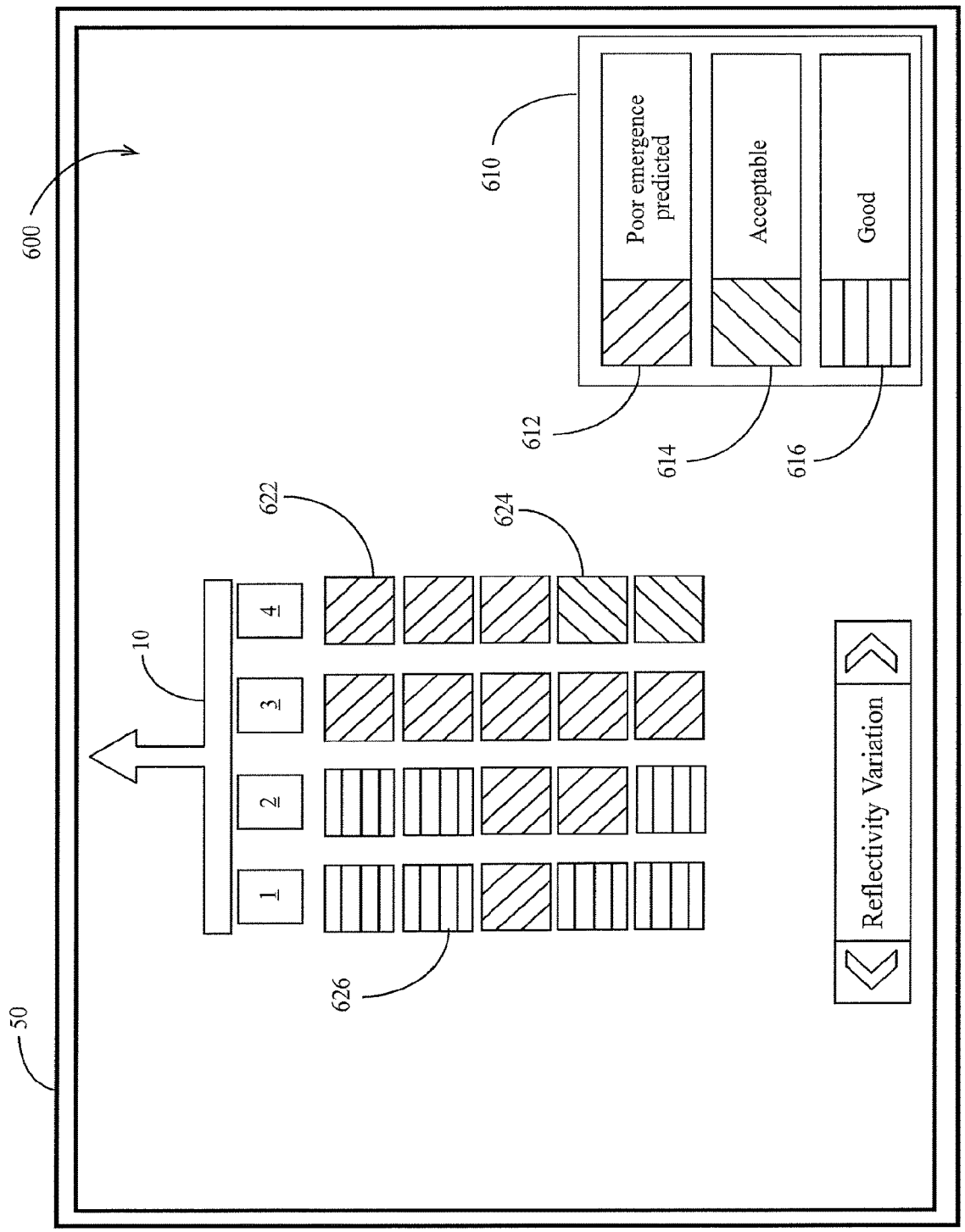
FIG. 6 illustrates an embodiment of a graphical display including a spatial map of reflectivity variation.

Referring to FIG. 5, the implement monitor 50 may display a soil data summary 500 displaying a representation (e.g., numerical or legend-based representation) of soil data gathered using the seed firmer 400 and associated sensors. The soil data may be displayed in windows such as a soil moisture window 510 and soil temperature window 520. A depth setting window 530 may additionally show the current depth setting of the row units of the implement, e.g., the depth at which the seed firmers 400 are making their respective measurements. A reflectivity variation window 550 may show a statistical reflectivity variation during a threshold period (e.g., the prior 30 seconds) or over a threshold distance traveled by the implement (e.g., the preceding 30 feet). The statistical reflectivity variation may comprise any function of the reflectivity signal (e.g., generated by each reflectivity sensor 350) such as the variance or standard deviation of the reflectivity signal. The monitor 50 may additionally display a representation of a predicted agronomic result (e.g., percentage of plants successfully emerged) based on the reflectivity variation value. For example, values of reflectivity emergence may be used to look up a predicted plant emergence value in an empirically-generated database (e.g., stored in memory of the implement monitor 50 or stored in and updated on a remote server in data communication with the implement monitor) associating reflectivity values with predicted plant emergence. Referring to FIG. 6, the reflectivity variation may be displayed spatially on a spatial reflectivity variation map 600 displayed (e.g., on the implement monitor 50 or remote computer). Areas of the field may be associated with graphical representations 622, 624, 626 (e.g., pixels or blocks) associated by color or pattern with subsets 612, 614, 616, respectively of a legend 610. The subsets may correspond to numerical ranges of reflectivity variation. The subsets may be named according to an agronomic indication empirically associated with the range of reflectivity variation. For example, a reflectivity variation below a first threshold at which no emergence failure is predicted may be labeled "Good"; a reflectivity variation between the first threshold and a second threshold at which predicted emergence failure is agronomically unacceptable (e.g., is likely to affect yield by more than a yield threshold) may be labeled "Acceptable" a reflectivity variation above the second threshold may be labeled "Poor emergence predicted".

Each window in the soil data summary 500 preferably shows an average value for all row units ("rows") at which the measurement is made and optionally the row unit for which the value is highest and/or lowest along with the value associated with such row unit or row units Selecting (e.g., clicking or tapping) each window preferably shows the individual (row-by-row) values of the data associated with the window for each of the row units at which the measurement is made.

Image Capture

Figure 7:
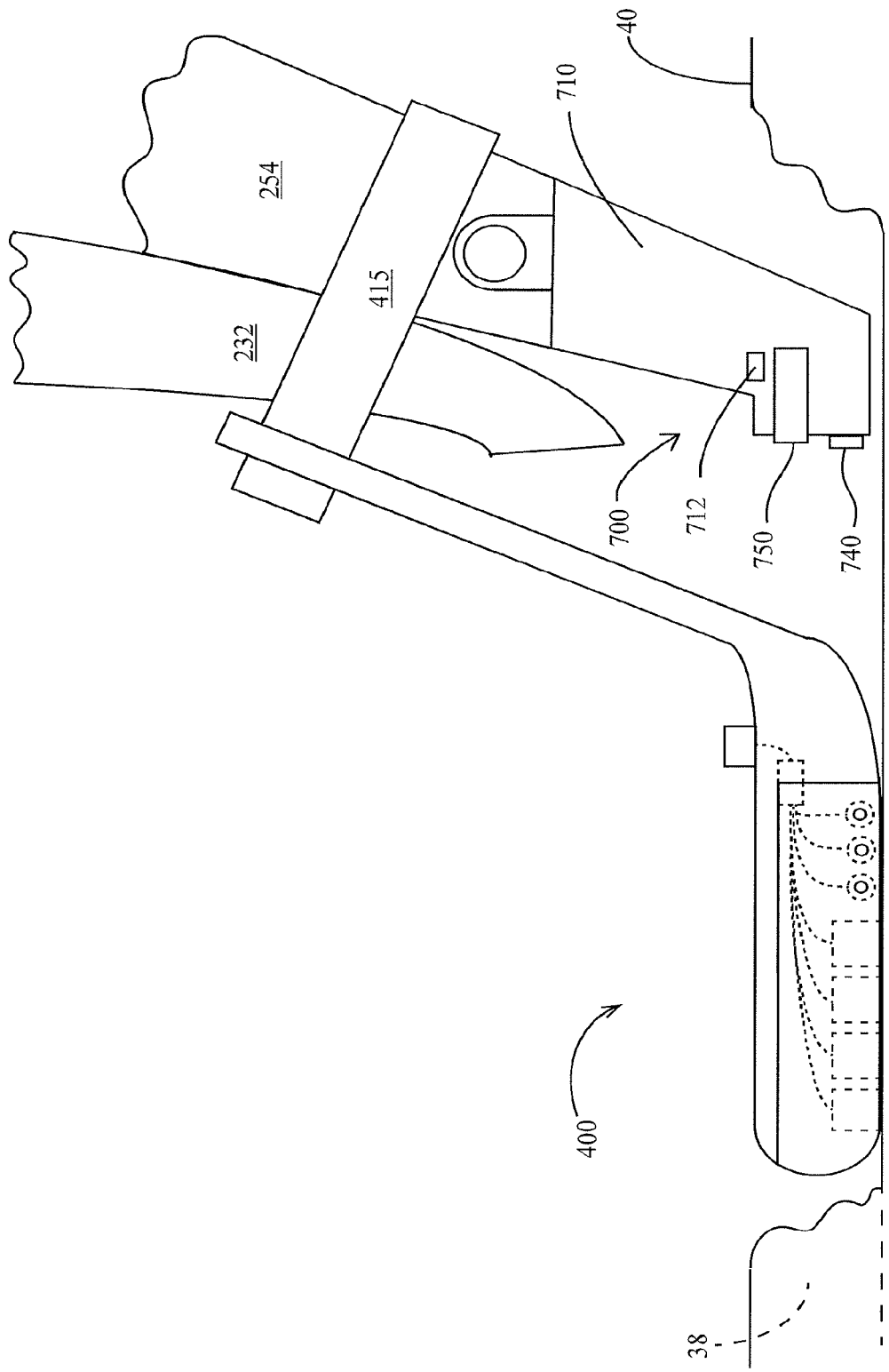
FIG. 7 illustrates a row unit incorporating an embodiment of an image capture apparatus.

Turning to FIG. 7, an image capture apparatus 700 is illustrated incorporating a camera 750 mounted to an extension 710. In one embodiment, extension 710 can be a guard and/or scraper (also known as a frog), which is used to keep opening discs 244 spread and/or to clean dirt from opening disc 244. The extension 710 may be removably mounted to a portion of the row unit such as a lower end of the shank 254 or to bracket 415. The camera 750 is preferably oriented to capture an image of the trench, and may be oriented rearward (e.g., opposite the direction of travel) and disposed at least partially inside the trench 38 (e.g., at least partially below the surface. It should be appreciated that the camera 750 is mounted forward of the closing system 236 and rearward of a leading edge of the opening discs 244 (e.g., at least partially laterally between the opening discs). In embodiments in which the camera 750 is adjacent to the opening discs 244, one or more wear-resistant guards 712 (comprised, e.g., of tungsten carbide or other wear-resistant material) is preferably mounted to either side of the extension 710 and preferably extend laterally outward such that their laterally terminal ends are disposed between the camera 750 and the opening discs 244 to protect the camera from contact with the opening discs. Alternatively, wear-resistant guards 712 can be mounted on either side of camera 750 on extension 710 and oriented parallel to the direction of travel and have a thickness such that camera 750 is not in contact with opening discs 244 or trench 38. A light source 740 (e.g., LED) is preferably mounted to the extension 710 and preferably disposed to illuminate the trench 38 and/or soil surface 40 to improve the quality of image capture. The image or images captured by the camera 750 preferably include the sidewalls of the trench, the bottom of the trench and/or the upper surface of the soil surface 40. The camera may be disposed forward of the seed firmer 400 as illustrated and may be disposed to capture an image of seeds. The camera may be a video camera and/or still image camera and is preferably in data communication with the implement monitor 50 for transmission of images to the implement monitor for display to the user and/or association with a location (e.g., geo-referenced location) in the field at which the images are captured and for storage in memory of the implement monitor and/or on a remote server.

Figure 8:
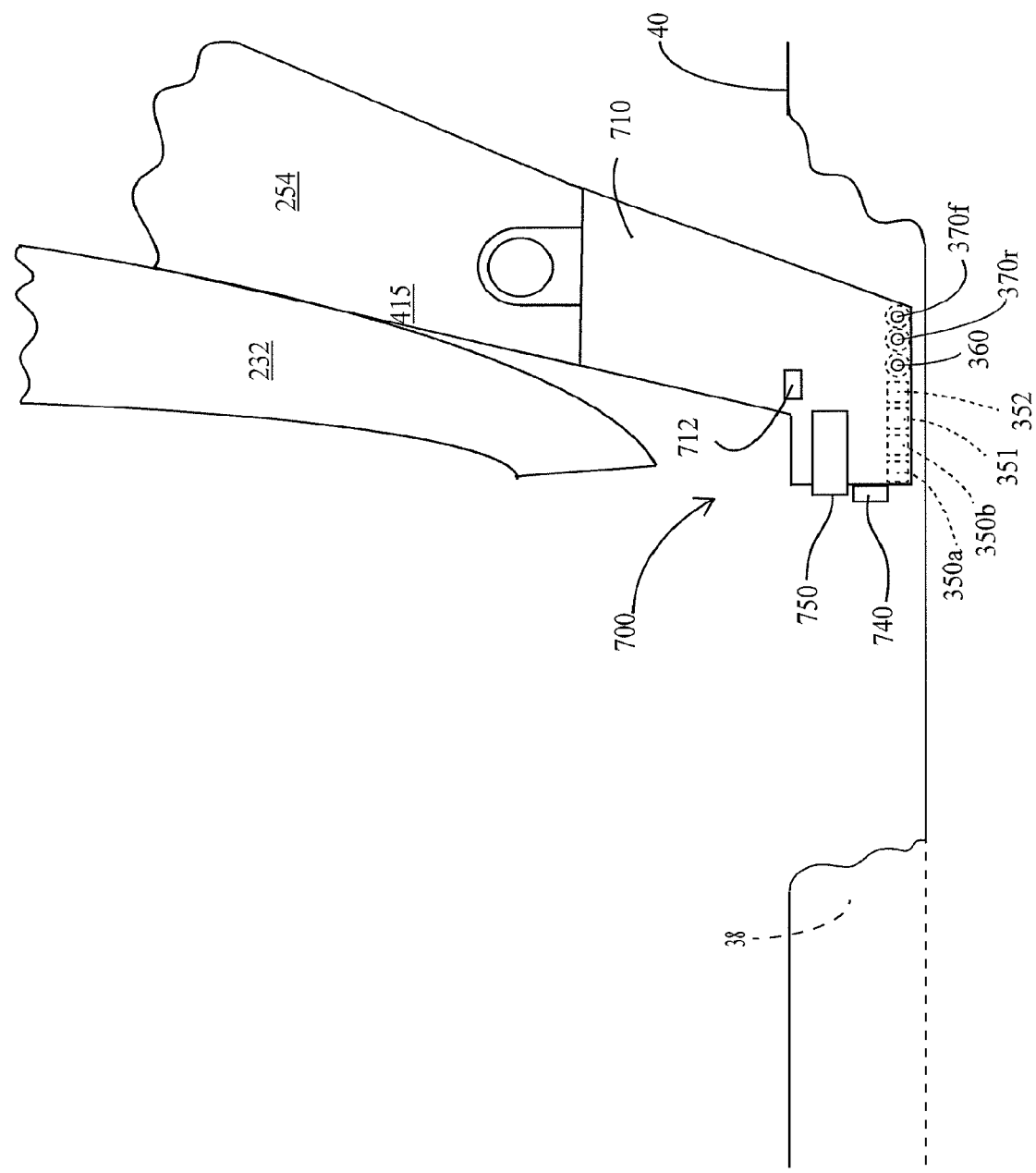
FIG. 8 is a side elevation view of an embodiment of a shank extension incorporating sensors and an image capture apparatus.

In an alternative embodiment as shown in FIG. 8, any of the sensors (e.g., 350, 351, 352, 360, and/or 370) described as being disposed on the seed firmer type soil engaging component 400 may be disposed on soil engaging component comprising a shank extension 710. The sensors can be mounted on the side of the extension 710 to be in contact with the sidewalls of trench 38, or the sensors can be mounted on the bottom of the extension 710 to be in contact with the bottom of trench 38. It should be appreciated that pairs of the multiple sensors 350, 351, 352, 360, 370 may be disposed vertically on the extension 710 to provide measurements at different depths in the seed trench 38. The multiple sensors may be used on extension 710 in conjunction with camera 750 or without the camera 750.

The benefit of disposing the sensors on extension 710 is that signal variation generated by a seed as firmer 400 passes over the seed does not need to be subtracted out of the signal. This simplifies the processing of the signal especially when seeds are planted close together, such as with soybeans. Also, the sidewalls of trench 38 are smoother than the bottom of trench 38, which results in less signal variability, which also simplifies the processing of the signal. Also, when sensors are mounted on extension 710, a greater force can be applied so that the sensor has an increased soil contact for increased measurement. As can be appreciated, the firmer 400 has a maximum force that can be applied based on seed to soil contact in given soil conditions so that the seed is planted at a desired depth with desired seed to soil contact and/or to prevent movement of seeds. Also, extension 710 can better protect the sensor and/or camera from rocks during planting as compared to firmer 400.

Figure 9:
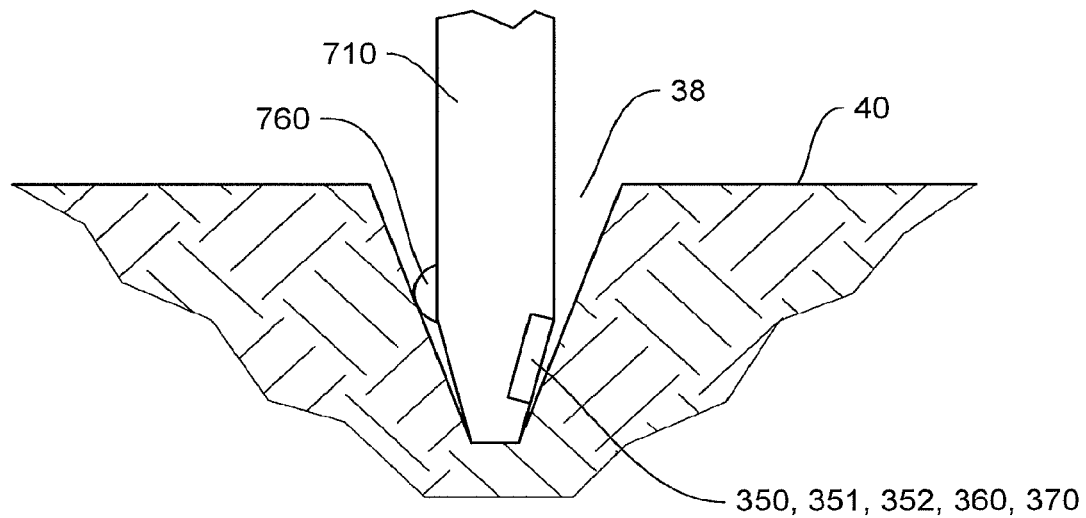
FIG. 9 is an elevation view of the shank extension of FIG. 8 showing a biasing member.
Figure 10:
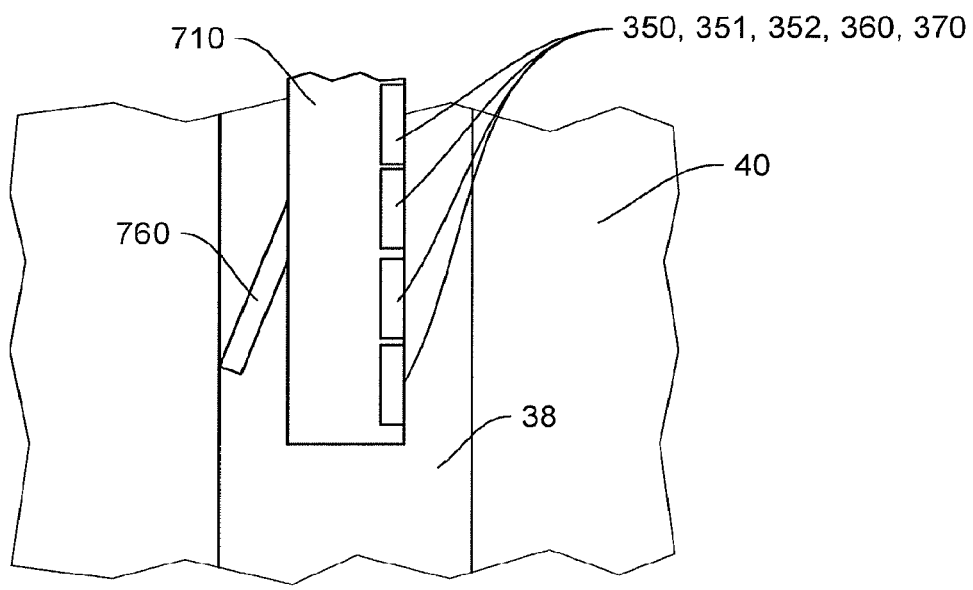
FIG. 10 is a top partial plan view of the shank extension of FIG. 8 showing an alternative embodiment of a biasing member.

The extension 710 may include a biasing member 760 disposed to bias the extension in contact with the sidewalls of the trench 38 to provide a more consistent engagement with the soil and thus a more uniform signal by minimizing side-to-side movement of the extension 710 within the trench 38. Examples of various types of biasing members 760 may include, but are not limited to, wing bump, such as shown in FIG. 9, or a whisker, wishbone or lever spring, such as shown in FIG. 10. The biasing member 760 can also be disposed between extension 710 and camera 750 and wear-resistance guards 712 to keep the wear-resistance guards 712 in contact with trench 38 and to keep the camera lens clean from accumulating dirt. In these embodiments, extension 710 acts as a stop for the sensor and/or camera. Alternatively, biasing members 760 can be disposed on the side of the seed firmer 400 (not shown).

It should be appreciated that if the extension 710 is a guard/scraper, the frictional forces between opening discs 244 and extension 710 can generate heat due to friction, which can cause the extension to approach 150° C. Accordingly, thermal insulation may be desirable between the sensors 350, 351, 352, 360, 370 and the body of the extension 710 to minimize thermal transfer between the body of the extension and the sensors disposed therein or thereon.

Figure 11:
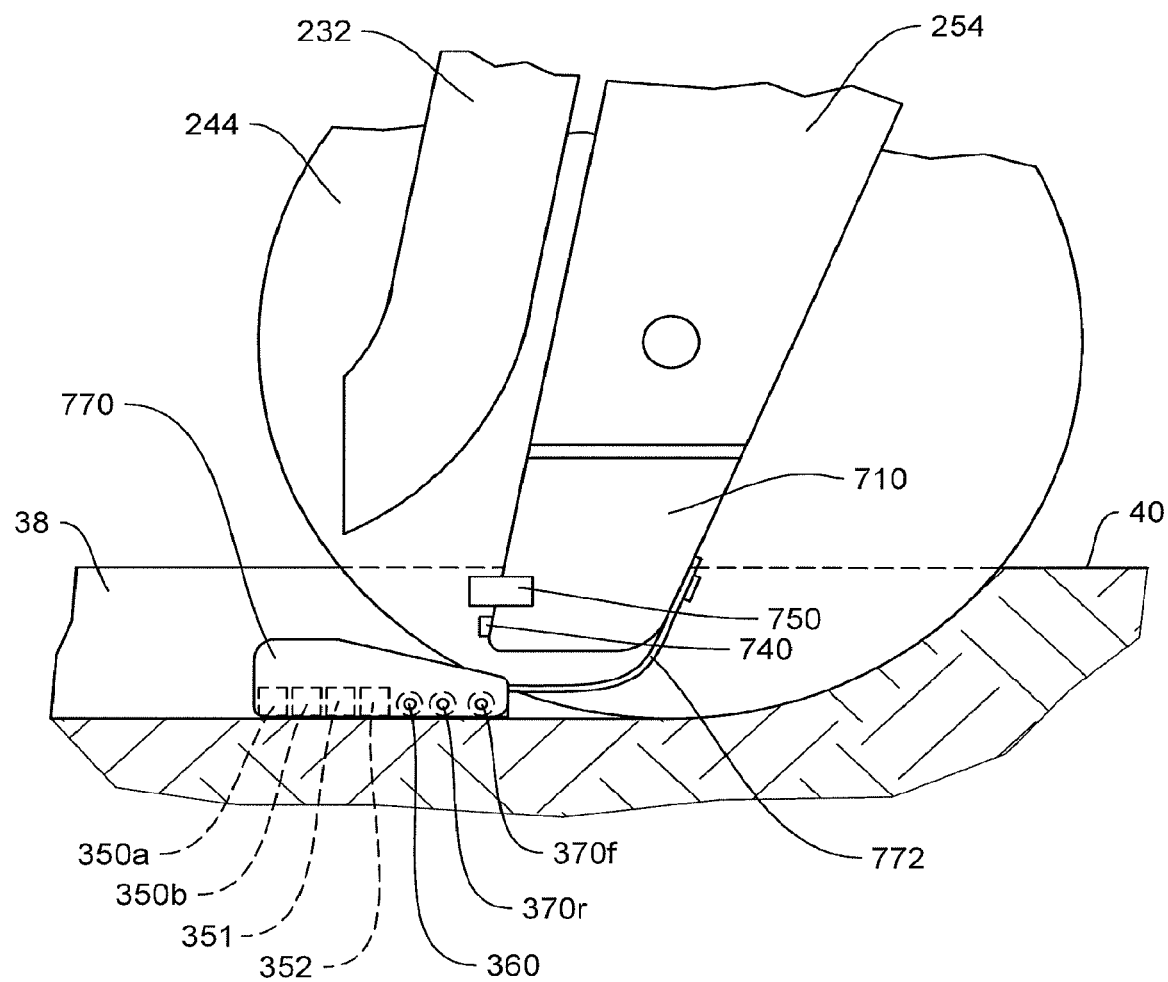
FIG. 11 is a side elevation view of a trailing member with sensors in combination with a shank extension with an image capture apparatus.

In yet another alternative embodiment, as shown in FIG. 11, the sensors 350, 351, 352, 360, 370 may be disposed on the bottom or sidewalls of a soil engaging component comprising a trailing member 770 secured to the shank 254 or to the shank extension 710 by a resilient arm 772 such that it is below and rearward of the shank 254 or extension 710 but forward of the trajectory of the seeds being deposited by the seed tube. Alternatively, the resilient arm 772 can be a living hinge (not shown). The resilient arm 772 biases the trailing member 770 into the bottom of the seed trench 38 to ensure consistent and uniform contact with the soil. Additionally, the trailing member 770 may incorporate any of the side biasing members 760 as previously described to minimizing side-to-side movement of the extension 710 within the trench 38 to provide more consistent engagement with the soil and thus a more uniform signal. As shown in FIG. 11, the trailing member 770 is disposed slightly behind opening discs 244 to allow dirt to flow around the trailing member.

Figure 12:
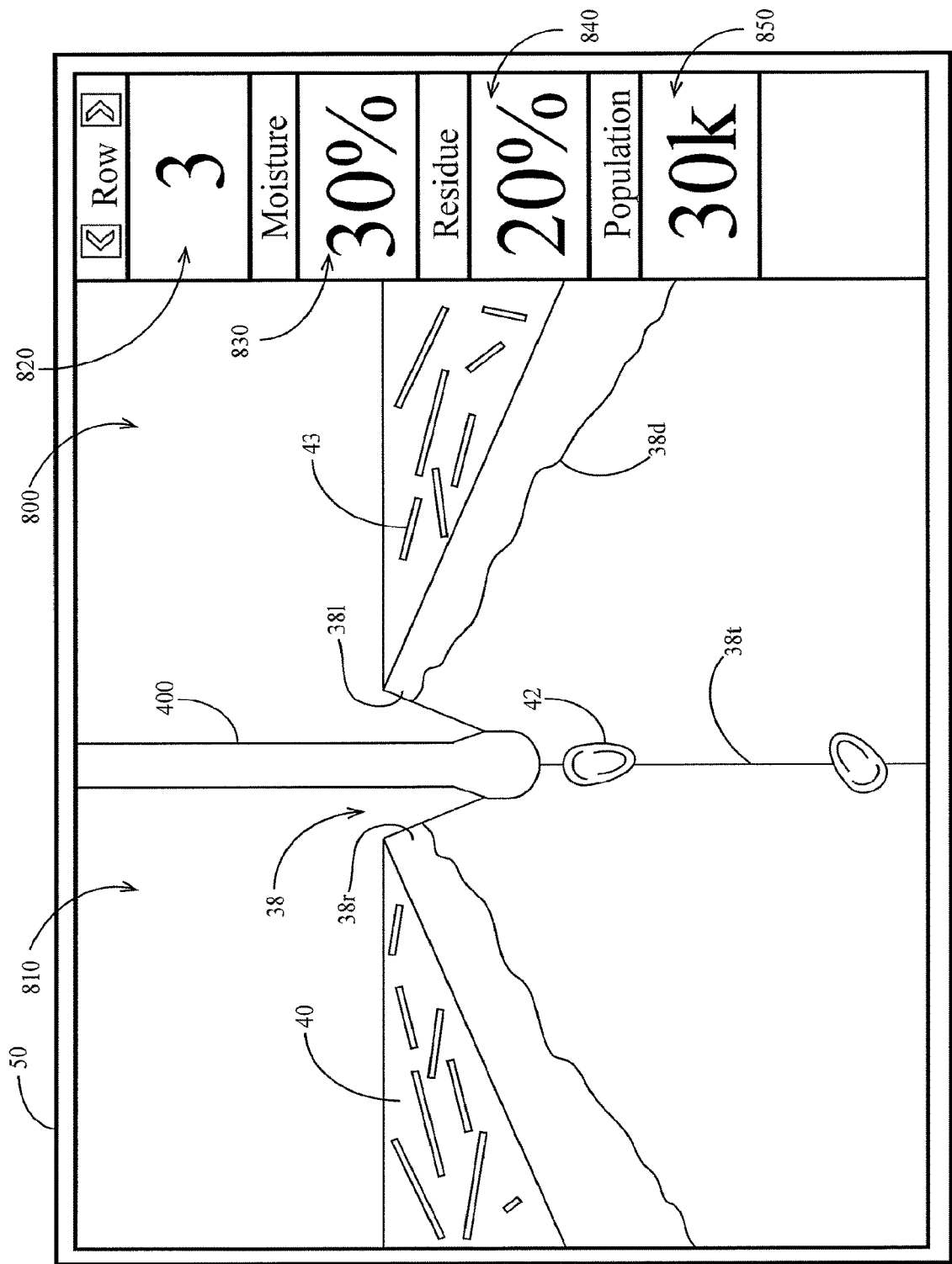
FIG. 12 illustrates an embodiment of a graphical display including an image captured by the image capture apparatus of FIG. 7, 8 or 11.

Turning to FIG. 12, the implement monitor 50 preferably displays a screen 800 including an image 810 (e.g., video or still image) including the soil surface 40, residue 43 on the soil surface, the trench 38 including sidewalls 38r, 381 and trough 38t thereof, and seeds 42 disposed in the bottom of the trench.

The screen 800 preferably includes a row identification window 820 which identifies which row is associated with the displayed image. Selecting one of the arrows in the row identification window 820 preferably commands the monitor 50 to load a new screen including an image associated with another, different row of the implement (e.g., captured by a second image capture apparatus associated with that other, different row).

The screen 800 preferably includes numerical or other indications of soil or seed data which the monitor 50 may determine by analyzing one or more images 810 or a portion or portions thereof.

Soil data measurement window 830 preferably displays a soil moisture value associated with the soil in the trench 38. The soil moisture value may be based upon an image analysis of the image 810, e.g., the portion of the image corresponding to the sidewalls 38r, 38l. Generally, the image 810 may be used to determine a moisture value by referencing a database correlating image characteristics (e.g., color, reflectivity) to moisture value. To aid in determining the moisture value, one or more images may be captured at one or more wavelengths; the wavelengths may be selected such that a statistical correlation strength of image characteristics (or an arithmetic combination of image characteristics) with moisture at one or more wavelengths is within a desired range of correlation strength. A wavelength or amplitude of light waves generated by the light source 740 may also be varied to improve image quality at selected image capture wavelengths or to otherwise correspond to the selected image capture wavelengths. Alternatively, a soil moisture value may be based upon capacitive moisture from sensor 351 or soil moisture tension from electronic tensiometer sensor 352. In some implementations, the trench may be divided into portions having different estimated moistures (e.g., the portions of the sidewall 38l above and below the moisture line 38d) and both moistures and/or the depth at which the moisture value changes (e.g., the depth of moisture line 38d) may be reported by the screen 800. It should be appreciated that the moisture values may be mapped spatially using a map similar to the map shown in FIG. 6. It should be appreciated that a similar method and approach may be used to determine and report soil data other than moisture (e.g., soil temperature, soil texture, soil color) based on one or more captured images.

Agronomic property window 840 preferably displays an agronomic property value (e.g., residue density, trench depth, trench collapse percentage, trench shape) which may be estimated by analysis of the image 810. For example, a residue density may be calculated by the steps of (1) calculating a soil surface area (e.g., by identifying and measuring the area of a soil surface region identified based on the orientation of the camera and the depth of the trench, or based on the color of the soil surface), (2) calculating a residue coverage area by determining an area of the soil surface region covered by (e.g., by identifying a total area of the soil surface covered by residue, where residue may be identified by areas having a color lighter than a constant threshold or more than a threshold percentage lighter than an average color of the soil surface region), and (3) dividing the residue coverage area by the soil surface area.

Planting criterion window 850 preferably displays a planting criterion such as seed spacing, seed singulation, or seed population. The planting criterion may be calculated using a seed sensor and the algorithms disclosed in U.S. Pat. No. 8,078,367, incorporated by reference ("the '367 patent"). In some implementations, algorithms similar to those disclosed in the '367 patent may be used in conjunction with a distance between seeds calculated with reference to the image 810. For example, the monitor 50 may (1) identify a plurality of seeds in the image 810 (e.g., by identifying regions of the image having a range of colors empirically associated with seeds); (2) identify one or more image distances between adjacent seeds (e.g., by measuring the length of a line on the image between the centroids of the seeds); (3) convert the image distances to "real space" distances using a mathematical and/or empirical relationship between distances extending along the trench in the image and corresponding distances extending along the actual trench; (4) calculate a planting criterion (e.g., seed population, seed spacing, seed singulation) based on the "real space" distances and/or the image distances.

Figure 13:
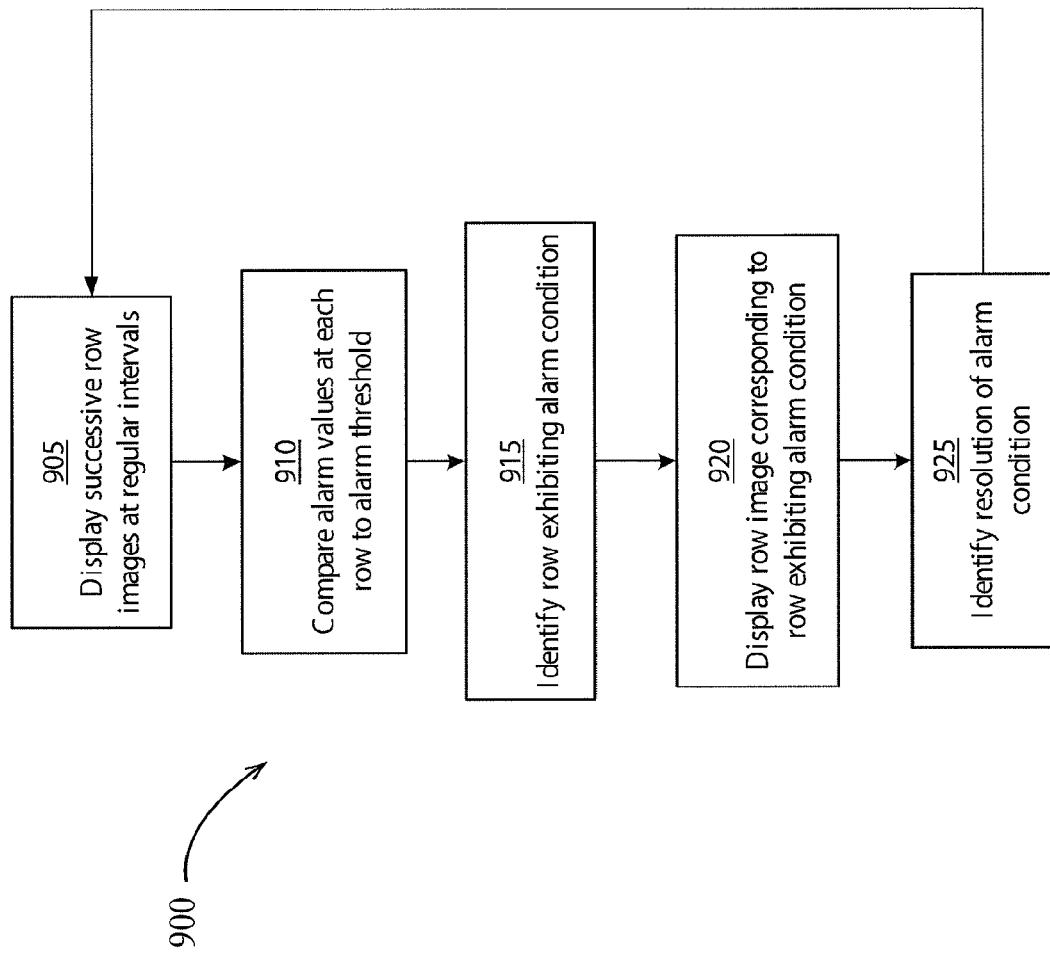
FIG. 13 illustrates an embodiment of a row image selection process.

Turning to FIG. 13, an exemplary process 900 for selecting a row image to display on the screen 800 is illustrated. It should be appreciated that because multiple row units may incorporate an image capture apparatus, it may be undesirable to simultaneously display images from all such row units. Instead, at step 905, the monitor 50 preferably displays successive row images (i.e., still or video images captured by successive row units) by displaying a new row image a regular interval (e.g., 10 seconds, 30 seconds, one minute). For example, a first still image or video stream from a first image capture apparatus at a first row unit may be displayed until the expiration of a first regular interval, whereupon a second still image or video stream from a second image capture apparatus at a second row unit may be displayed until the expiration of a second regular interval. Step 910 is preferably carried out simultaneously with step 905; at step 910 the monitor 50 preferably compares an alarm value at each row unit to an associated alarm threshold. The alarm value may correspond to a soil measurement value (e.g., soil moisture, soil temperature soil texture, soil color, soil reflectivity, soil reflectivity variation) which may be estimated based on analysis of the row image or measured by another soil characteristic sensor associated with the row unit; the alarm value may correspond to an agronomic property or planting criterion (e.g., residue density, trench collapse, trench shape, trench depth, seed spacing, seed singulation, seed population, fertilizer flow rate) which may be estimated based on analysis of the row image or measured by another agronomic property sensor (such as a seed sensor, fertilizer flow rate sensor, trench depth sensor). The alarm threshold may comprise a selected constant value of the alarm value or a statistical function (e.g., one or more standard deviation above or below the mean or average) of the alarm value reported to the monitor during a preceding period or during operation in a specified area (e.g., 30 seconds, 30 feet of travel, the entire field associated with the operation). At step 915, the monitor 50 preferably identifies a row exhibiting an alarm condition (e.g., at which the alarm value has exceeded the alarm threshold). At step 920, the monitor 50 preferably displays (e.g., on the screen 800) the row image captured by the image capture apparatus associated with the row unit exhibiting the alarm condition. The monitor 50 may optionally indicate a graphical representation of the alarm condition adjacent to the row image, e.g. in a separate window indicating the alarm or by adding an attention-drawing indication (e.g., a red border) to a window (e.g., soil data measurement window 830, agronomic property window 840). At step 925, the monitor 50 preferably identifies a resolution of the alarm condition (e.g., by enabling the user to cancel the alarm or by determining that the alarm condition is no longer active) and preferably returns to step 905.

In one embodiment, the depth of planting can be adjusted based on soil properties measured by the sensors and/or camera so that seeds are planted where the desired temperature, moisture, and/or conductance is found in trench 38. A signal can be sent to the depth adjustment actuator 380 to modify the position of the depth adjustment rocker 268 and thus the height of the gauge wheels 248 to place the seed at the desired depth. In one embodiment, an overall goal is to have the seeds germinate at about the same time. This leads to greater consistency and crop yield. When certain seeds germinate before other seeds, the earlier resulting plants can shade out the later resulting plants to deprive them of needed sunlight and can disproportionately take up more nutrients from the surrounding soil, which reduces the yield from the later germinating seeds. Days to germination is based on a combination of moisture availability (soil moisture tension) and temperature.

In one embodiment, moisture can be measured by volumetric water content or soil moisture tension. The depth can be adjusted when a variation exceeds a desired threshold. For example, the depth can be adjusted deeper when the volumetric water content variation is greater than 5% or when the soil moisture tension variation is greater than 50 kPa.

In another embodiment, the depth of planting can be adjusted until good moisture is obtained. Good moisture is a combination of absolute and moisture variation. For example, good moisture exists when there is greater than 15% volumetric water content or soil moisture tension and less than 5% variation in volumetric water content or soil moisture tension. A good moisture can be greater than 95%.

In another embodiment, a data table can be referenced for combinations of moisture and temperature and correlated to days to emergence. The depth can be controlled to have a consistent days to emergence across the field by moving the depth up or down to combinations of temperature and moisture that provide consistent days to emergence. Alternatively the depth can be controlled to minimize the days to emergence.

In another embodiment, the depth can be adjusted based on a combination of current temperature and moisture conditions in the field and the predicted temperature and moisture delivery from a weather forecast This process is described in US. Patent Publication No. 2016/0037709, which is incorporated herein by reference.

In any of the foregoing embodiments for depth control for moisture, the control can be further limited by a minimum threshold temperature. A minimum threshold temperature (for example 10° C. (50° F.)) can be set so that the planter will not plant below a depth where the minimum threshold temperature is. This can be based on the actual measured temperature or by accounting for the temperature measured at a specific time of day. Throughout the day, soil is heated by sunshine or cooled during night time. The minimum threshold temperature can be based on an average temperature in the soil over a 24 hour period. The difference between actual temperature at a specific time of day and average temperature can be calculated and used to determine the depth for planting so that the temperature is above a minimum threshold temperature.

The soil conditions of conductivity, moisture, temperature, and/or reflectance can be used to directly vary planted population (seeds/acre), nutrient application (gallons/acre), and/or pesticide application (lb./acre) based off of zones created by organic matter, soil moisture, and/or electrical conductivity.

In another embodiment, any of the sensors or camera can be adapted to harvest energy to power the sensor and/or wireless communication. As the sensors are dragged through the soil, the heat generated by soil contact or the motion of the sensors can be used as an energy source for the sensors.

The foregoing description is presented to enable one of ordinary skill in the art to make and use the invention and is provided in the context of a patent application and its requirements. Various modifications to the preferred embodiment of the apparatus, and the general principles and features of the system and methods described herein will be readily apparent to those of skill in the art. Thus, the present invention is not to be limited to the embodiments of the apparatus, system and methods described above and illustrated in the drawing figures, but is to be accorded the widest scope consistent with the spirit and scope of the appended claims.

What is claimed is:

1. A system for measuring soil properties, the system comprising:
   a planter row unit of a planter, the planter row unit including:
      a shank extension;
      at least one sensor coupled to the shank extension, the at least one sensor configured to measure at least one soil property of soil worked by the planter row unit and/or of soil in a trench opened by the planter row unit;
      a seed tube configured to dispense seeds into the trench opened by the planter row unit, the seed tube positioned relative to the shank extension to dispense the seeds in the trench after the at least one sensor measures the at least one soil property; and
      a camera coupled to the shank extension and arranged to capture images of the soil worked by the planter row unit and/or the trench opened by the planter row unit.

2. The system of claim 1, wherein the planter row unit includes first and second opening discs configured to open the trench, the first and second opening discs coupled to a shank, which is coupled to the shank extension; and
   wherein the shank extension is disposed generally between the first and second opening discs.

3. The system of claim 2, wherein the at least one sensor includes one or more of a reflectivity sensor, a temperature sensor, an electrical conductivity sensor, a moisture sensor, and/or an electronic tensiometer sensor.

4. The system of claim 1, wherein the at least one sensor is configured to be disposed at least partly within the trench opened by the planter row unit to measure the at least one soil property of the soil worked by the planter row unit and/or the soil in the trench opened by the planter row unit.

5. The system of claim 4, wherein the camera is configured to be disposed at least partly within the trench opened by the planter row unit to capture the images of the trench.

6. The system of claim 1, further comprising a light source coupled to the planter row unit, the light source arranged to illuminate the trench and/or the soil worked by the planter row unit.

7. The system of claim 1, further comprising thermal insulation disposed between the shank extension and the at least one sensor, to thereby inhibit thermal transfer between the shank extension and the at least one sensor.

8. The system of claim 1, wherein the at least one sensor includes at least one ear disposed on the at least one sensor and extending away from the at least one sensor, the at least one ear configured to engage the soil worked by the planter row unit and/or the soil in the trench opened by the planter row unit.

9. The system of claim 8, wherein the at least one ear of the at least one sensor is constructed from a thermally conductive material.

10. The system of claim 1, further comprising at least one processor configured to:
receive the measured at least one soil property of the soil worked by the planter row unit and/or of the soil in the trench opened by the planter row unit;
receive one or more of the images captured by the camera; and
cause display, on a monitoring device, a representation of the received at least one soil property and the received one or more of the images captured by the camera.

11. The system of claim 10, wherein the at least one processor is further configured to cause display, on the monitoring device, at least one of: a row identifier, a soil moisture value, and/or at least one agronomic property value based on analysis of at least one of the images.

12. A system for measuring soil properties, the system comprising:
a shank extension configured to couple to a shank of a planter row unit of an agricultural planter, the planter row unit operable to open a seed trench;
a camera coupled to the shank extension and configured to capture images of the seed trench opened by the planter row unit;
at least one sensor coupled to the shank extension, the at least one sensor configured to measure at least one soil property of soil within the seed trench opened by the planter row unit; and
a seed tube configured to dispense seeds into the seed trench, the seed tube positioned relative to the shank extension to dispense the seeds in the seed trench after the at least one sensor measures the at least one soil property.

13. The system of claim 12, wherein the shank extension is configured to position the at least one sensor at least partly within the seed trench opened by the planter row unit to measure the at least one soil property of the soil within the seed trench.

14. The system of claim 13, wherein the at least one sensor includes one or more of a reflectivity sensor, a temperature sensor, an electrical conductivity sensor, a moisture sensor, and/or an electronic tensiometer sensor.

15. The system of claim 14, wherein the shank extension is configured to position the camera at least partly within the seed trench opened by the planter row unit to the capture images of the seed trench.

16. The system of claim 12, further comprising thermal insulation disposed between the shank extension of the planter row unit and the at least one sensor, to thereby inhibit thermal transfer between the shank and the at least one sensor.

17. The system of claim 12, wherein the at least one sensor includes at least one ear disposed on the at least one sensor and extending away from the at least one sensor, the at least one ear configured to engage a portion of the trench opened by the planter row unit, to thereby measure the at least one soil property of the soil within the seed trench.

* * * * *